(12) United States Patent
Li et al.

(10) Patent No.: US 10,550,051 B2
(45) Date of Patent: Feb. 4, 2020

(54) ETHYLENE YIELD IN OXIDATIVE DEHYDROGENATION OF ETHANE AND ETHANE CONTAINING HYDROCARBON MIXTURES

(71) Applicant: North Carolina State University, Raleigh, NC (US)

(72) Inventors: Fanxing Li, Raleigh, NC (US); Luke M. Neal, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/422,743

(22) Filed: Feb. 2, 2017

(65) Prior Publication Data
US 2017/0226030 A1     Aug. 10, 2017

Related U.S. Application Data

(60) Provisional application No. 62/291,822, filed on Feb. 5, 2016.

(51) Int. Cl.
*C07C 5/327*     (2006.01)
*C07C 5/333*     (2006.01)
(Continued)

(52) U.S. Cl.
CPC ............ *C07C 5/42* (2013.01); *C07C 2523/34* (2013.01); *C07C 2523/835* (2013.01); *C07C 2523/889* (2013.01)

(58) Field of Classification Search
CPC ............ C07C 5/327; C07C 5/333; C07C 2/82
(Continued)

(56) References Cited

U.S. PATENT DOCUMENTS 4,737,595 A     4/1988 Jones et al.
4,777,313 A  *  10/1988 Sofranko ............... B01J 21/02
                                                              585/500
(Continued)

OTHER PUBLICATIONS

Peng, et al., Effect of methane co-feeding on the selectivity of ethylene produced from oxidative dehydrogenation of ethane with CO2 over a Ni—La/SiO2 catalyst, Journal of Energy Chemistry 22 (2013): 653-658.
(Continued)

*Primary Examiner* — Thuan D Dang
(74) *Attorney, Agent, or Firm* — Thomas|Horstemeyer, LLP

(57) ABSTRACT

Methods and systems are provided for oxidative dehydrogenation of a hydrocarbon feed stream to produce a product stream with improved ethylene yield. The methods can include the steps of (i) combining a recycle stream with the feed stream to form a reactor feed stream, (ii) contacting the reactor feed stream with an oxide-based redox catalyst to produce the product stream comprising ethylene and one or more byproducts selected from the group consisting of methane, ethane, other byproducts, and mixtures thereof, and (iii) removing all or a part of the methane and ethane from the product stream to produce the recycle stream. Systems for the oxidative dehydrogenation (ODH) of a hydrocarbon feed stream are also provided to produce a product stream with improved ethylene yield. The systems and methods can include an oxide-based redox catalyst, such as $Mg_6MnO_8$, $Cu_6PbO_8$, and $Ni_6MnO_8$.

16 Claims, 6 Drawing Sheets

(51) Int. Cl.
*C07C 2/82* (2006.01)
*C07C 5/42* (2006.01)

(58) Field of Classification Search
USPC .................................. 585/658, 661, 662, 663
See application file for complete search history.

(56) References Cited

U.S. PATENT DOCUMENTS

| | | | |
|---|---|---|---|
| 4,849,571 A | 7/1989 | Gaffney | |
| 6,518,476 B1 * | 2/2003 | Culp | ........................ C07C 2/84 585/655 |
| 2014/0371504 A1 † | 12/2014 | Stine | |

OTHER PUBLICATIONS

Nghiem, Xuan Son, Ethylene Production by Oxidative Coupling of Methane: New Process Flow Diagram Based on Adsorptive Separation, Dissertation, Technical University of Berlin (2014).

Eltron Research and Development, Oxidative Dehydrogenation of Methane and Ethane Using Catalytic Membrane Reactors, Tech Brief.

Edwards, et al., The OXCO process. The new concept for the production of olefins from natural gas. Fuel 71(1992): 325-334.

Sofranko, et al., Natural Gas to Gasoline: the ARCO GTG Process. Symposium on Methane Activation, Conversion and Utilization, International Congress of the Pacific Basin Societies, Honolulu, HI. (1989): 152-154.

Deboy, et al. Oxidative Coupling of Methane over Alkaline Earth Promoted La2O3. J. Chem. Soc., Chem. Commun. (1988): 982-984.

Henning, et al. Oxidative dehydration of ethane at short contact times: species and temperature profiles within and after the catalyst. Chem. Eng. Science 57 (2002): 2615-2625.

Chung, et al. Catalytic Oxygen Carriers and Process Systems for Oxidative Coupling of Methane Using the Chemical Looping Technology. Am Chem Soc (2016): 12750-12764.

Su, et al. Upper Bound on the Yield for Oxidative Coupling of Methane. J. Catal. 218:2 (2003): 321-333.

Mulla, et al. "Autothermal Oxidative Dehydrogenation of Ethane to Ethylene Using SrxLa1.0Nd1.0Oy Catalysts as Ignitors". Journal of Catalysis 2001, 1, 43-48.

Xu, et al. "Kinetic Modeling of Ethane Pyrolysis at High Conversion". Journal of Physical Chemistry 2011, 115, 10470-10490.

Yusuf, et al. "Effect of Promotors on Manganese Containing Mixed Metal Oxides for Oxidative Dehydrogenation of Ethane via a Cyclic Redox Scheme". ACS Catalysis 2017, 7, 5163-5173 (and supporting information).

\* cited by examiner
† cited by third party

ETHYLENE YIELD IN OXIDATIVE DEHYDROGENATION OF ETHANE AND ETHANE CONTAINING HYDROCARBON MIXTURES

CROSS-REFERENCE TO RELATED APPLICATIONS

This application claims priority to, and the benefit of, co-pending U.S. provisional application entitled "ETHYLENE YIELD IN OXIDATIVE DEHYDROGENATION OF ETHANE AND ETHANE CONTAINING HYDROCARBON MIXTURES" having Ser. No. 62/291,822, filed Feb. 5, 2016, the contents of which are incorporated by reference in their entirety.

STATEMENT REGARDING FEDERALLY SPONSORED RESEARCH

This invention was made with government support under Award Number DE-AR0000327 awarded by The Department of Energy. The government has certain rights in the invention.

TECHNICAL FIELD

The present disclosure generally relates to methods and systems for oxidative dehydrogenation of hydrocarbons.

BACKGROUND

Ethylene is a chemical precursor of significant commercial importance, for example as a raw material for the manufacture of polymers, ethylbenzene, styrene, and polystyrene, among other chemical products. The vast majority of ethylene commercially produced is derived from steam cracking of naphtha and/or ethane and/or propane. Ethylene may be obtained from the non-catalytic thermal cracking of saturated hydrocarbons, such as ethane and propane, and alternatively from thermal or steam cracking of heavier liquids such as naphtha and gas oil. Steam cracking produces a variety of other products, including diolefins and acetylene. The latter are costly to separate from the ethylene, usually by extractive distillation and/or selective hydrogenation to the corresponding mono-olefin, e.g. acetylene to ethylene. In addition, thermal cracking processes for olefin production are highly endothermic and sensitive to the quality of the feed stream. In traditional steam cracking, energy intensive separation steps would be used to remove some of the contaminants in the feed stream such as methane, hydrogen, CO, and C3 hydrocarbons. Some or all of these byproducts are frequently burned to partially offset the large energy deficit of the steam cracking process. The combustion of these byproducts as fuel produces significant $CO_2$ and or $NO_x$ emissions. Furthermore, all of these processes require a large consumption of fuel and the construction and maintenance of large, capital-intensive and complex cracking furnaces to supply the heat.

Existing steam cracking processes generate ethylene by raising the feed (ethane or other hydrocarbons) to high enough temperature (700-1000° C.) in furnace tubes to thermally crack the hydrocarbons into olefins, especially ethylene and secondarily propylene, plus a range of other hydrocarbons, hydrogen and coke. The residence time must be very short, at a level measured in milliseconds, and the effluent must be quenched immediately, in order to maximize the desired olefins and minimize the undesired byproducts. The pressure must be kept to a minimum, substantial steam dilution is required, and design features are critical for obtaining the best performance. As a result, the reaction conditions are very sensitive, and the furnaces are very expensive, with high fuel requirement due to both the high temperature and the high endothermicity of the cracking reactions. Frequent decoking is also a major requirement. Furthermore, furnace tubes must be replaced periodically.

Given the drawbacks of conventional steam cracking production of ethylene, significant research and effort has been invested in the development of alternative methods. One important alternative is to catalytically dehydrogenate ethane in the presence of oxygen to form ethylene. The process is called oxidative dehydrogenation (ODH). In this process, the product is largely limited to ethylene with small amounts of other byproducts such as methane, carbon monoxide, carbon dioxide, and other hydrocarbons. The effluent can also contain water (produced in the reaction plus whatever enters with the feed), residual ethane, some residual oxygen, and nitrogen if introduced with the oxygen (e.g., as air). The oxidative dehydrogenation (ODH) of ethane is thermodynamically favored and can be carried out at lower reaction temperatures that conventional steam cracking and without coke formation. Commercialization of ODH has been hindered low product selectivity at high ethane conversions. Further, the ODH byproducts, although not present in large enough amounts to warrant energy intensive separation, can be present in the feed and as byproducts of the ODH process. Separation can be energy intensive and, unlike steam cracking, ODH is energy efficient and does not require these byproducts (or a substitute fuel) to be burned to drive the process.

There remains a need for improved systems and methods for producing ethylene from ethane and ethane-containing fuels via oxidative dehydrogenation methods that do not produce or produce less of these byproducts.

SUMMARY

In various aspects, methods and systems are provided for the oxidative dehydrogenation of a hydrocarbon feed stream to produce a product stream with improved ethylene yield that overcome the aforementioned deficiencies. In various aspects, the feed stream includes about 1% to 10% methane. In various aspects, the feed stream includes about 25% ethane or less. In various aspects, the methods can include recycling methane in a recycle stream, wherein the yield of ethylene is higher than the yield of ethylene in the otherwise same system under the otherwise same conditions except where the methane is not recycled in the recycle stream. In various embodiments, the systems and methods work with a feed stream that contain essentially just ethane and methane. In some aspects, the feed stream is an ethane-containing stream from a liquefied natural gas separation unit. In other aspects, the feed stream is an ethane-containing feed stream from a stream cracker separation train.

In one or more embodiments, a method for the oxidative dehydrogenation of a hydrocarbon feed stream is provided to produce a product stream with improved ethylene yield. In various aspects, the method can include the steps of (i) combining a recycle stream with the feed stream to form a reactor feed stream, (ii) contacting the reactor feed stream with an oxide-based redox catalyst to produce the product stream comprising ethylene and one or more byproducts selected from the group consisting of methane, ethane, other byproducts, and mixtures thereof, and (iii) removing all or a part of the methane and ethane from the product stream to produce the recycle stream.

In one or more embodiments, a system for the oxidative dehydrogenation (ODH) of a hydrocarbon feed stream is provided to produce a product stream with improved ethylene yield. In various aspects, the system includes (i) an ODH reactor including an oxide-based redox catalyst, (ii) a separation train configured to receive a product stream from the ODH reactor and to separate the product stream into at least an ethylene stream, an ethane stream, and a methane stream; and (iii) a recycle stream configured to recycle all or a part of the ethane stream and/or the methane stream and configured to be combined with the product stream prior to entering the ODH reactor. In one or more aspects, the ODH reactor is a circulating fluidized bed reactor, a packed bed reactor, or a combination thereof. In some embodiments, the system can further include a liquefied natural gas separation unit configured to direct an ethane-containing stream into the feed stream.

In one or more embodiments, a system for the oxidative dehydrogenation (ODH) of a feed stream coming from a steam cracker is provide to produce a product stream with improved ethylene yield. The system can include (i) a steam cracker unit configured to receive a cracker feed stream and to produce a cracked stream; (ii) a separation train configured to receive the cracked stream and to separate the cracked stream into at least an ethylene stream, an ethane stream, and a methane stream; (iii) a reactor feed stream configured to receive all or a part of the methane and/or ethane; and (iv) an ODH reactor including an oxide-based redox catalyst and configured to receive the reactor feed stream to produce a product stream configured to be separated in the separation train. In one or more aspects, the ODH reactor is a circulating fluidized bed reactor, a packed bed reactor, or a combination thereof.

In various embodiments, the systems and methods include an oxide-based redox catalyst. In some aspects, the oxide-based redox catalyst is an oxide having the formula $R_6R'O_8$, wherein each R and R' are selected from Mg, Mn, Fe, Ni, Al, Cr, Cu, and Co. In one or more aspects, the oxide-based redox catalyst is $Mg_6MnO_8$, $Cu_6PbO_8$, and $Ni_6MnO_8$. In one or more embodiments, the oxide-based redox catalyst includes a promoter, such as a promoter selected from the group Li, Na, B, Sm, Ga, Ti, W, Mo, V, Nb, Cr, K, Cs, Rb, P, and As.

Other systems, methods, features, and advantages of methods and systems for the oxidative dehydrogenation of a hydrocarbon feed stream to produce a product stream with improved ethylene yield will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
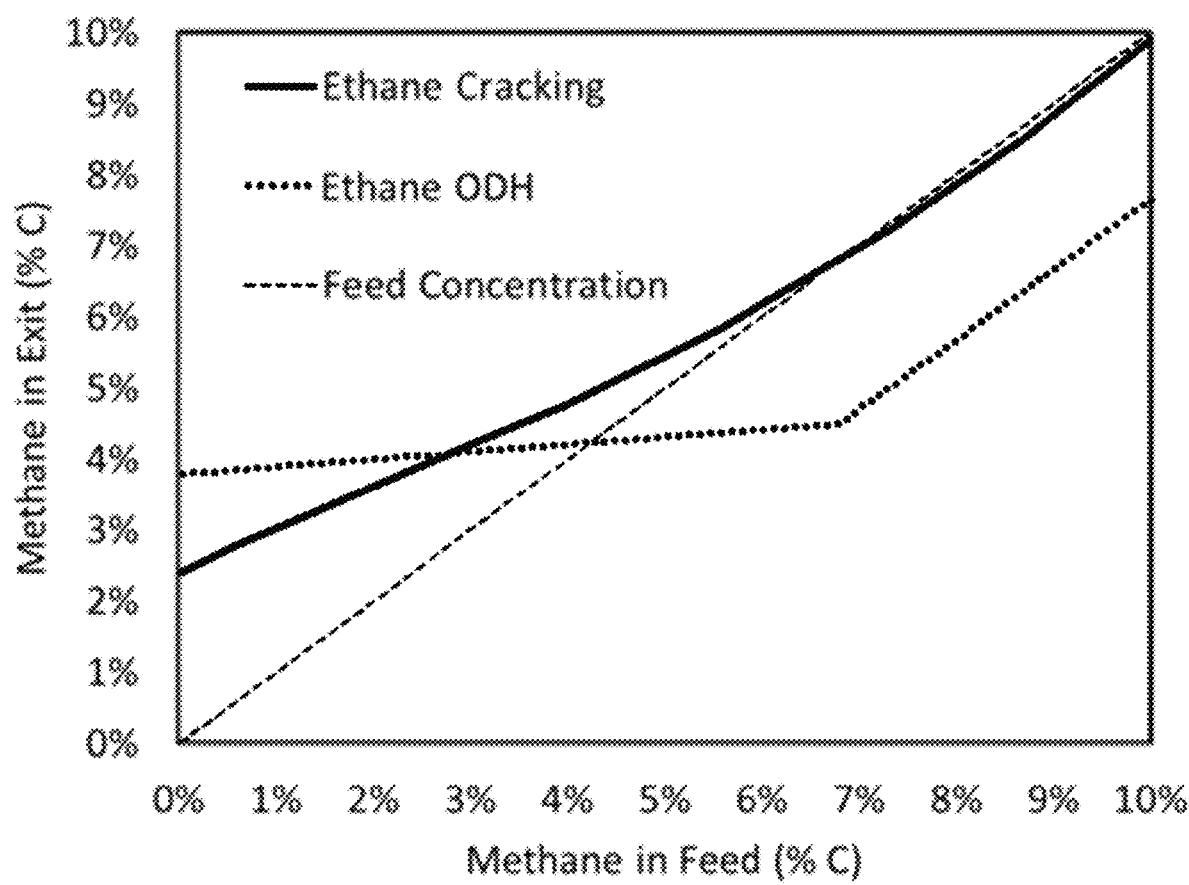
FIG. 1 is a graph of the amount of methane in the reactor exit (% C) along the vertical axis versus the amount of methane in the ethane feed (% C) for traditional ethane cracking and for ethane oxidative dehydrogenation (ODH) at 850° C., a gas hourly space velocity (GHSV) of 3000 h$^{-1}$, and 80% hydrocarbon feed.

Systems and methods for improving ethylene yield and overall system efficiency in the oxidative dehydrogenation (ODH) of ethane and methane rich hydrocarbon mixtures are designed. The system contains a circulating fluidized bed reactor, a system of fluidized bed reactors, or a series of fixed bed reactors with gas switching using a redox catalyst/oxygen transport agent, and a product gas separation train. In these systems and methods all or part of the methane, propane, propylene, butanes, and or other minor gaseous hydrocarbon byproducts, as well as hydrogen and or CO byproducts can be recycled into the feed of the ODH reactor. Due to the properties of the oxide-based redox catalyst (such as those described in PCT/US2015/051661, the contents of which are incorporated herein by reference in their entirety) the hydrocarbons are converted to ethylene and other valuable products, such as 1, 3-butadiene and pyrolysis gasoline.

Methane, which represents a notable fraction of the product stream, is of low value and is often converted into heat along with CO and $H_2$. Although, one use can be in conjunction with the ODH system describe in PCT/US2015/051661, with proper catalyst selection, the invention is applicable to ethane ODH processes in general. The oxidative dehydrogenation of ethane to ethylene over a chemical looping catalyst has several advantages vs. the commonly used steam cracking process as laid out in PCT/US2015/051661. The systems and methods described herein enhance these advantages, by simplifying the separation of products, increasing the yield of ethylene, and making the process more energy self-sufficient without additional emissions.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'"

Unless otherwise specified, where a percentage of a hydrocarbon in a stream is given, the percentage is a carbon percentage (% C).

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

Systems and Methods

Various systems and methods are provided for the oxidative dehydrogenation of ethane and ethane-containing feed streams to produce ethylene. In some aspects, the systems and methods are capable of achieving high ethylene selectivity and/or high ethylene yield even in embodiments where the ethane feed stream includes impurities such as methane, propane, butane, or other oxidative dehydrogenation byproducts. In various aspects, the systems and methods are capable of operating with high ethylene selectivity and/or high ethylene yield with little or no methane production, e.g. the methane is substantially consumed and converted into olefins. In various aspects, the systems and methods are capable of producing ethylene and other valuable byproducts such as benzene, pygas, and/or 1,3-butadiene with little or no methane production. The systems and methods offer several advantages over steam cracking and over conventional ODH systems that typically require pure feeds and/or are incapable of achieving both high ethylene selectivity and high yield. The systems and methods can, in various embodiments, operate without significantly larger or costlier reactors as compared to these conventional processes. The systems and methods can also operate continuously and with fluctuations in the concentration of the feed stream.

Figure 2:
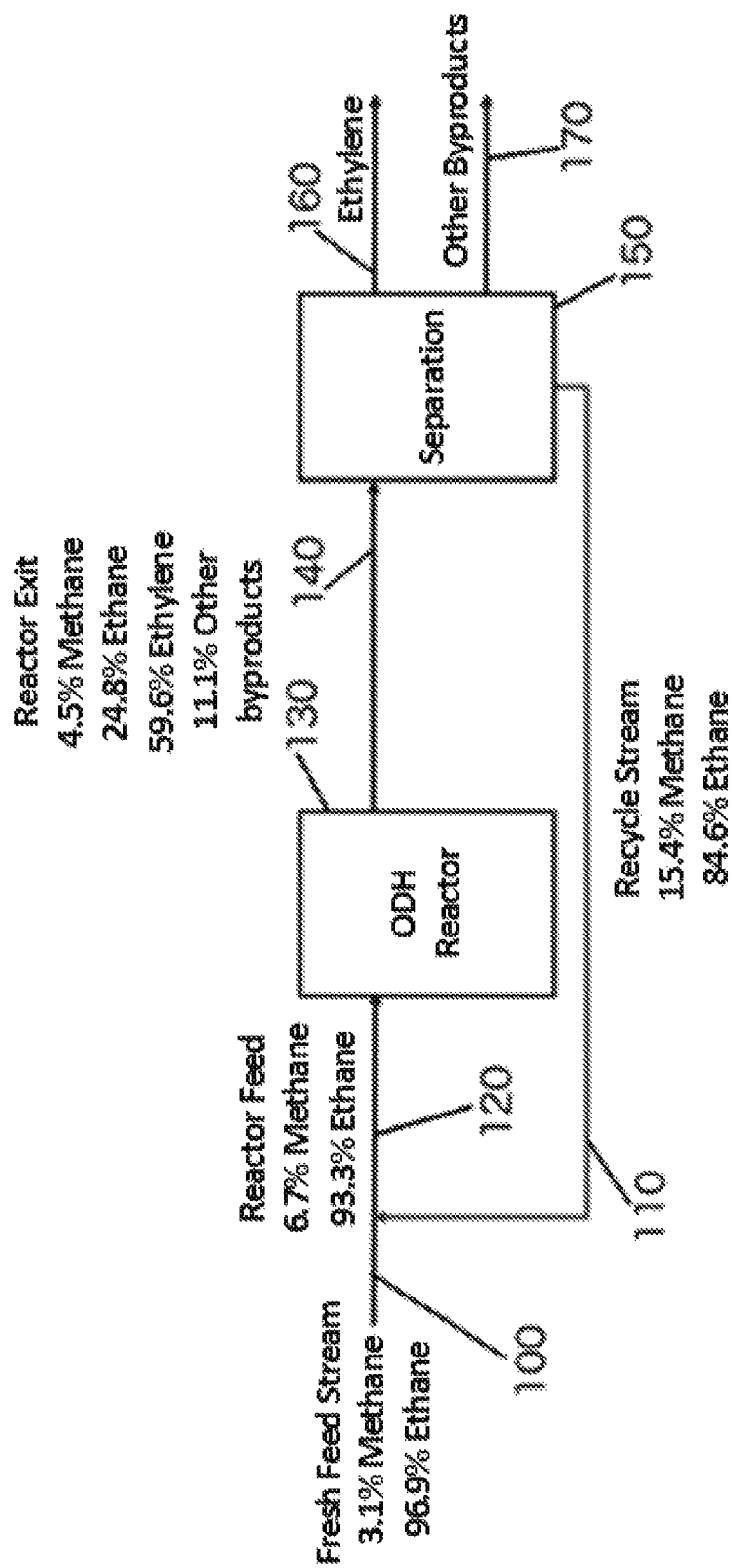
FIG. 2 is a schematic of one embodiment of an oxidative dehydrogenation (ODH) process with recycle.

A general embodiment of the systems and methods for ODH of ethane to ethylene is described in FIG. 2. The percentage compositions for each stream depicted in FIG. 2 are percent carbon (% C) of the stream, and although these are exemplary compositions, the exact amounts may vary depending upon the exact nature of the feed stream, the operating conditions, and/or the specific catalyst used. The hydrocarbon feed stream 100 can include a mixture of essentially just methane and ethane, e.g. about 96.9% ethane and 3.1% methane. The hydrocarbon feed stream 100 can be combined with a recycle stream 110 to produce a reactor feed stream 120. The recycle stream 110 can be rich in methane, e.g. containing a greater percentage of methane than the hydrocarbon feed stream 100. In various embodiments, the recycle stream 110 can have a methane content of about 5%, 10%, 15%, or more. The reactor feed stream 120 can enter into an ODH reactor 130. A variety of ODH reactor designs are envisioned as described below, and those skilled in the art will easily recognize other reactor designs that may be employed. All such designs are intended to be encompassed by the disclosure and accompanying claims. Inside the ODH reactor 130 the reactor feed stream 120 can contact an oxide-based redox catalyst (not pictured) to produce a product stream 140. The product stream 140 can be rich in ethylene, e.g. an ethylene content of about 50%, 55%, 60%, 65%, or more. The product stream 140 can flow into a separation unit 150 where the product stream can be separated to produce an ethylene output stream 160. The product stream 140 can also be separated to produce a stream of other byproducts 170 such as higher olefins. All or a part of the methane and/or unreacted ethane from the product stream 140 can be separated to produce the recycle stream 110.

The methods can include ODH of an ethane-containing feed stream which contains up to 75 vol. % other gaseous components including but not limited to methane, propane, other hydrocarbon, $H_2$, and/or CO in which the unreacted methane, hydrogen, CO, and/or other byproducts are recycled, moving the method towards energy sufficiency and improving the yield of ethylene and other valuable hydrocarbons. The ethane-containing feed stream can contain up to 75 vol. % other gaseous components, e.g. about 10 vol % to 75 vol %, about 10 vol % to 60 vol %, about 15 vol % to 60 vol %, about 20 vol % to 60 vol %, or about 30 vol % to 60 vol %. The methods can include ODH of an ethane-containing feed stream having at least 1%, 2%, 3%, or more of methane. The ethane-containing feed stream can contain up to 5%, 10%, or 15% methane. In some embodiments, the methane is recycled to extinction to produce ethylene and other valuable byproducts when the methane content in the feed-stream is about 4%, 3.5%, 3.1%, 3.0%, 2.5%, or less. The methane content in the feed stream can be about 1% to 10%, about 2% to 5%, or about 2% to 4%.

As methane is a low value product it would typically be burned to partially offset large energy deficits of the steam cracking process. In the systems and methods provided herein, the methane can be consumed in the reactor to produce ethylene and other valuable products, allowing up to 90%, 95%, 99%, or 100% recycle, even in the presence of significant amounts of methane in the feedstock. This results in higher net yields of ethylene from the same amount of feedstock, and helps consume the methane without emission of additional $CO_2$. This is especially useful for ODH, as the superior energy efficiency reduces or eliminates the need for methane as a fuel gas. In some embodiments at least 20%, 30%, 40%, 50%, 60%, 70%, 80%, 90%, 95%, 98%, 99%, 99.9%, or 100% of the methane is recycled in the ODH reactor.

Additionally the systems and methods can be configured to recycle heavier hydrocarbons that are separated from the ethylene product stream. These hydrocarbons, such as propane, propylene and butanes are a nuisance in traditional steam cracking of ethane as they can cause severe coke accumulation and produce low-value methane. Although these byproducts can be valuable in a pure state, separation is prohibitively expensive. Thus, they are often burned as fuel gas. In traditional co-feed ethane ODH systems, these heavier hydrocarbons are too susceptible to deep oxidation to $CO_x$ to be efficiently converted to ethylene. In ODH there is limited need for fuel gas. When recycled into the ODH reactor, the redox agent allows significant heavy hydrocarbon impurities in the feed stream while limiting coke formation. As the redox agent also actively consumes methane that is generated by the cracking of these hydrocarbons, it is feasible to completely recycle these streams into the ODH reactor. This recycle, thus, produces additional ethylene while eliminating the need for costly separation of minor $C_3$ and $C_4$ products, or the production of additional $CO_2$ emissions from burning them as fuel gas. In some embodiments all or at least 50%, 60%, 70%, 80%, 90%, or more of one or more of the heavier hydrocarbons can be recycled in the ODH reactor.

Oxidative Dehydrogenation (ODH) Reactor

The systems and methods can include a variety of oxidative dehydrogenation (ODH) reactors. The ODH reactor can be a circulating fluidized-bed reactor, a packed bed reactor, or a combination thereof.

The ODH reactor can be a fluidized-bed reactor. A fluidized bed reactor can have high heat removal. A fluidized-bed reactor may result in greater isothermicity, avoidance of hot spots, and may also allow the feeds to be introduced separately, without pre-mixing. Various fluidized-bed reactor systems can be used, including dense bed (from gently bubbling up to turbulent bed), highly expanded bed ("fast fluid bed" or "circulating fluid bed"), entrained flow ("riser" or "downer"), or combinations. Heat removal can be to a heat transfer fluid or steam generation, through coils submerged in the bed and/or freeboard (above the bed), through the vessel wall, from a connected vessel with the catalyst particles transferred from one vessel to the other, etc.

Another fluidized bed system can be a "separated red/ox" fluidized bed system, also called a circulating fluidized bed system, where the ethane can be oxidatively dehydrogenated by the oxygen contained in the catalyst in one vessel, and the [O]-depleted catalyst can be transferred to a second vessel to replenish its oxygen. Then the oxygen-rich catalyst can be returned to the oxydehydrogenation reactor. In some embodiments, the ODG reactor can also include two or more packed bed reactors where the flow through each bed is switched from ODH mode, where the ethane can be oxidatively dehydrogenated by the oxygen contained in the catalyst, and regeneration mode, where oxygen rich air is passed through the bed to regenerate the catalyst therein.

Figure 3:
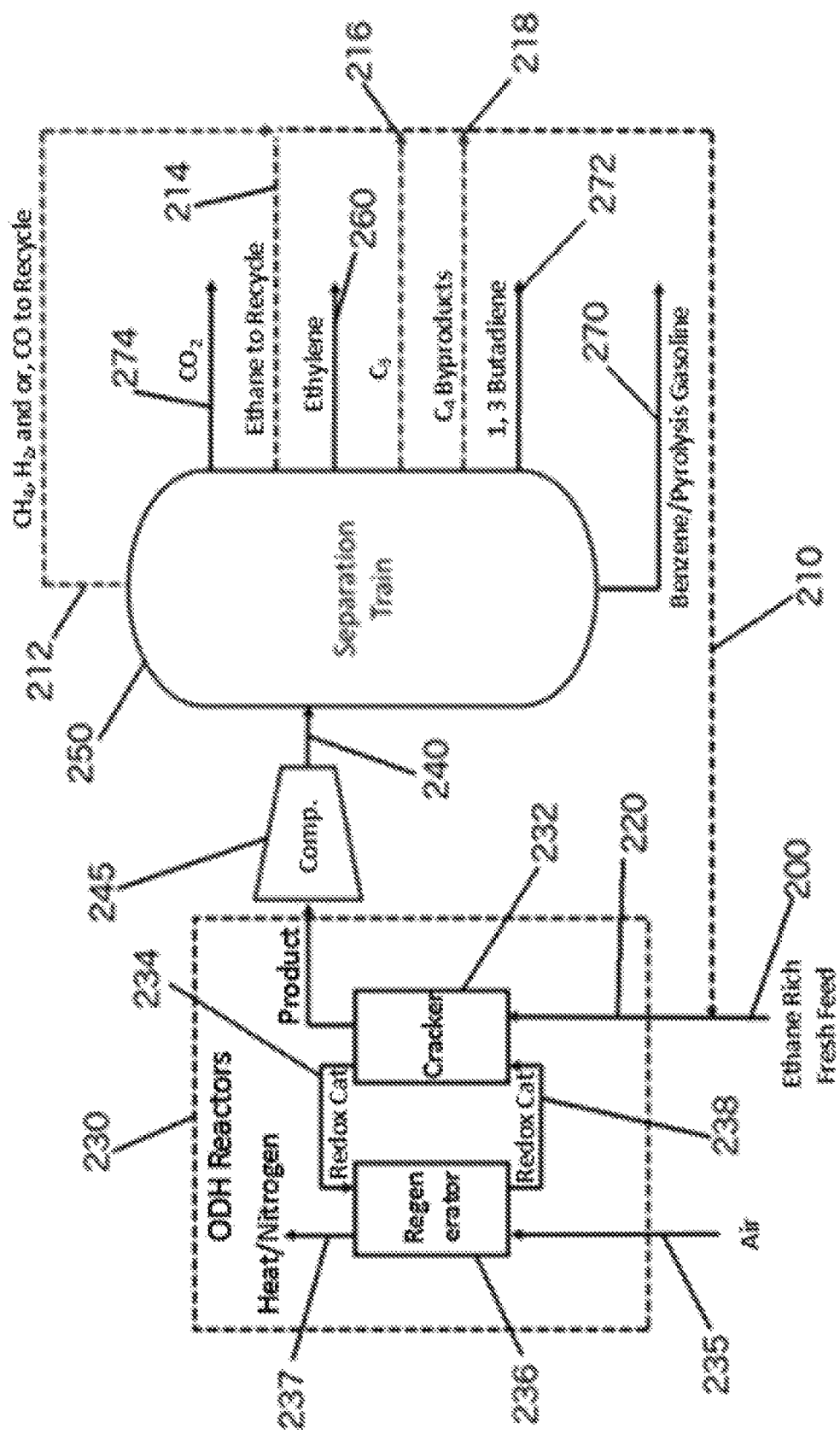
FIG. 3 is a schematic of one embodiment of a circulating fluidized oxidative dehydrogenation (ODH) reactor.

FIG. 3 depicts one embodiment of a system and method using a circulating fluidized bed ODH reactor 230. The hydrocarbon feed stream 200 is combined with the recycle stream 210 to form the reactor feed stream 220. The reactor feed stream 220 passes into the circulating fluidized bed ODH reactor 230. The reactor feed stream 220 can enter into a cracker 232 to contact the oxide-based redox catalyst to produce the product stream 240. The oxygen-depleted catalyst can exit the cracker 232 via line 234 to a regenerator 236 to be regenerated. For example, an oxygen-rich air source can enter the regenerator 236 via line 235. Heat, nitrogen, and/or unreacted oxygen can exit the regenerator 236 via line 237.

The product stream 240 leaving the circulating fluidized bed ODH reactor 230 can be compressed via a compressor 245 before entering the separation train 250. Ethylene can be removed from the separation train 250 via line 260. Other valuable products can be removed such as benzenes/pyrolysis gasoline via 270 and 1,3-butadiene via 272 as well as $CO_2$ via 274. The lighter byproducts such as methane as well as $H_2$ and/or CO can be separated via line 212 to produce the recycle stream 210. Additionally, unreacted ethane can be separated via line 214 to produce the recycle stream 210. Other low-value byproducts can be separated such as C3 byproducts via line 216 and C4 byproducts via line 218 to produce the recycle stream 210. All or a part of the byproduct streams 212-218 can be recycled individually or in combination to form the recycle stream 210.

Figure 4:
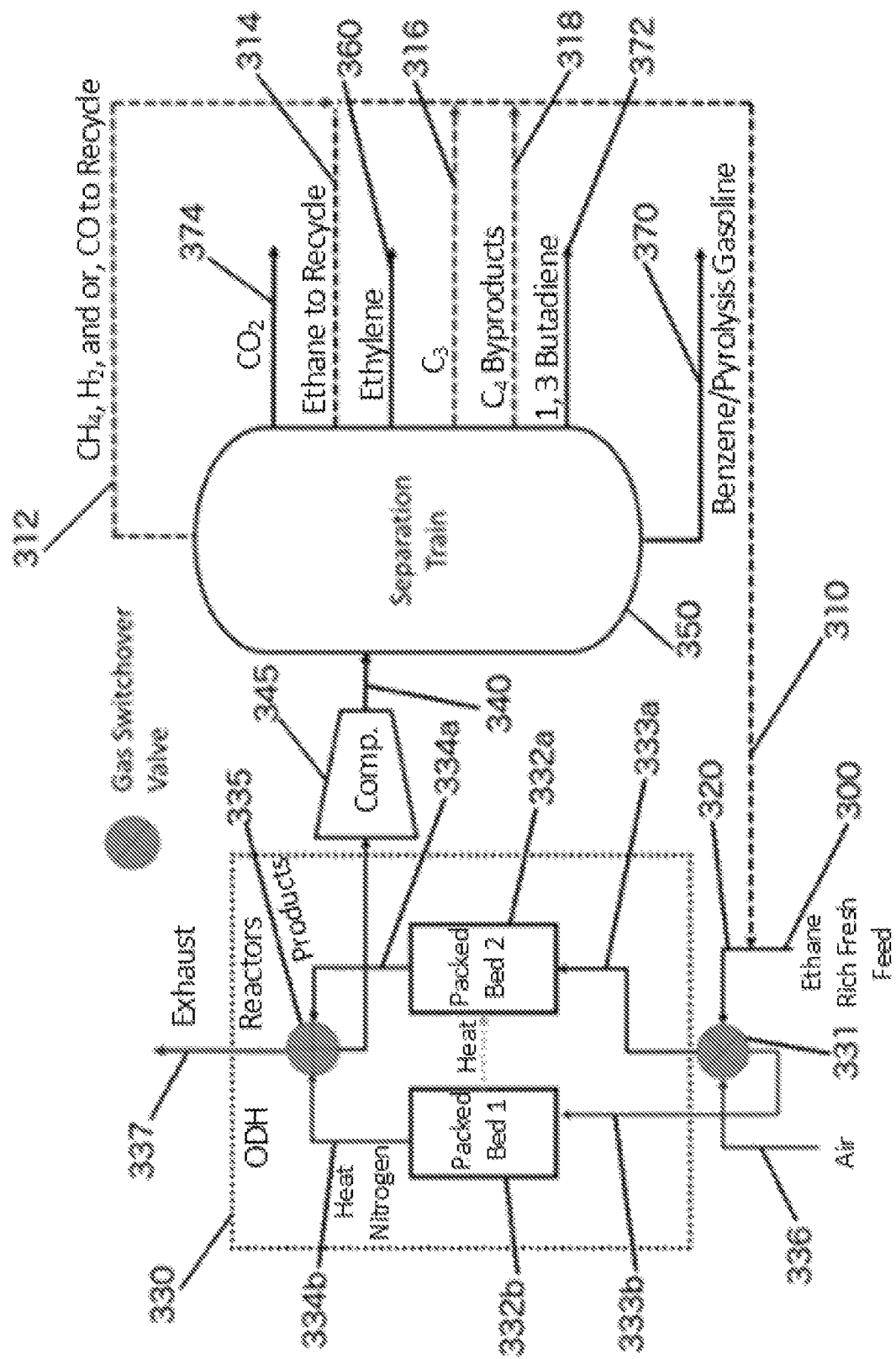
FIG. 4 is a schematic of one embodiment of an oxidative dehydrogenation (ODH) reactor having two packed beds and a gas switchover to change the packed bed from regeneration mode to ODH mode.

FIG. 4 depicts one embodiment of a system and method using a pair of packed bed reactors as the ODH reactor 330. The hydrocarbon feed stream 300 is combined with the recycle stream 310 to form the reactor feed stream 320. The reactor feed stream 320 passes through a first gas switchover valve 331 and, in the configuration depicted, is directed to a first packed bed reactor 332a via line 333a where it contacts the oxide-based redox catalyst that passes through line 334a to a second gas switchover valve 335. In the configuration depicted, the gas switchover valve 335 directs the flow from line 334a to produce the product stream 340. In the configuration depicted, the second packed bed reactor 332b is in regeneration mode. The oxygen rich air passes through line 336 to the first gas switchover valve 331 and is directed to the second packed bed reactor 332b via line 333b. After replenishing the catalyst therein, the exhaust is directed via line 334b to the second gas switchover valve 335 and through the exhaust 337. By switching the first gas switchover valve 331 and second gas switchover valve 335, the flow can be swapped such that the reactor feed stream 320 is directed to the second packed bed reactor 332b, and the product is directed through line 334b to the produce stream 340 via the second gas switchover valve 335. By switching the first gas switchover valve 331 and second gas switchover valve 335, the first packed bed reactor 332a is in regeneration mode.

The product stream 340 leaving ODH reactor 330 can be compressed via a compressor 345 before entering the separation train 350. Ethylene can be removed from the separation train 350 via line 360. Other valuable products can be removed such as benzenes/pyrolysis gasoline via 370 and 1,3-butadiene via 372 as well as $CO_2$ via 374. The lighter byproducts such as methane as well as $H_2$ and/or CO can be separated via line 312 to produce the recycle stream 310. Additionally, unreacted ethane can be separated via line 314 to produce the recycle stream 310. Other low-value byproducts can be separated such as C3 byproducts via line 316 and C4 byproducts via line 318 to produce the recycle stream 310. All or a part of the byproduct streams 312-318 can be recycled individually or in combination to form the recycle stream 310.

Oxidative Dehydrogenation (ODH) Catalyst

A variety of oxide-based redox catalyst can be used in the systems and methods described herein. The oxide-based redox catalyst can include one or more of those described in PCT/US2015/051661. The ODH catalyst can be a mixed metal oxide, for example a mixed manganese oxide such as $Mg_6MnO_8$, $NaB_2Mg_4Mn_2O_4$, $NaB_2Mn_2Mg_4O_{11.5}$, $Mg_6MnO_8$, $NaMn_2O_4$, $LiMn_2O_4$, $Mg_3Mn_3B_2O_{10}$, $Mg_3(BO_3)_2$. The ODH catalyst can include $Mg_6MnO_8$, $Cu_6PbO_8$ and $Ni_6MnO_8$. The ODH catalyst can have a cubic crystal structure. The ODH catalyst can be a mixed ionic-electronic conductor. The ODH catalyst include 8 an oxide having the formula $R_6R'O_8$, wherein each R and R' are Mg, Mn, Fe, Ni, Al, Cr, Cu, or Co. The oxide-based redox catalyst can further contain a promoter such as Li, Na, B, Sm, Ga, Ti, W, Mo, V, Nb, Cr, K, Cs, Rb, P, and As.

For ethane ODH in general the catalyst can contain transition and other metal oxides, or mixed metal oxides that exhibit facile internal transport of oxygen, and redox kinetics in the temperature range of interest (350° C.-1000° C.). Through either inherent activity or the use of dopants such as alkali and alkali earth oxides such as Na, Li, K, Ca, Ba, and Sr, the mixed oxide can be selective toward partial oxidation of hydrocarbons vs. deep oxidation or coke formation. Such single or mixed oxides may include, but are not limited to, samarium oxides, terbium oxides, vanadium oxides, molybdenum oxides, perovskite structured mixed oxides such as lanthanum lithium ferrite, lithium ferrite, B-site deficient perovskite with $(AA')_{n+1}(BB')_nO_{3n+1}$ (A and A' independently selected from Ba, Ca, La, Eu, Sr, Ce, and B and B' independently selected from Fe, Mn, Ni, Al, Cr, Cu, Co), manganese magnesium mixed oxides. Other catalyst dopants can be included such as platinum group metals or lanthanum chloride to improve activity towards other hydrocarbons, including, but not limited to improved activity for oxidative coupling of methane; and add additional dopants to counter increased coke formation kinetics of the heaver hydrocarbons in the feed.

Separation Unit

The ethylene products and other minor gases and byproducts can be separated by a variety of gas separation units known to those skilled in the art. The ethylene product may be separated from the residual ethane, any heavy byproducts, light byproducts and residual gases, plus impurities that boil close to the product ethylene and the ethane that can be recycled, by means known to those skilled in the art. The methane can be separated and recycled. The separation train can starts with the hot product stream being quenched and cooled down, and heavy fractions being condensed and separated. Thereafter, the product stream can be compressed and/or dried before it enters separation train. The compression can be done in a number of stages up to a pressure of about 30 bar or more, e.g. about 30 bar to 40 bar.

The product stream can be separated in the separation train into the $C_2$ minus fraction, which is routed to the cold section for further separation, and the $C_{3+}$ fraction. $C_2$ minus and $C_{3+}$ fractions are separated in sequences into specified products.

Ethane and Ethane-Containing Hydrocarbon Feed Source

The systems and methods include oxidative dehydrogenation of ethane or an ethane-containing hydrocarbon source to produce ethylene. The hydrocarbon feed stream can be pure ethane, a mixture of essentially ethane and methane, or a mixture of ethane with other impurities or byproducts such as methane, carbon monoxide, hydrogen, propane, butane, and mixtures thereof. The feed stream can come from any number of sources, including natural gas or an ethane rich byproduct stream of a pyrolysis plant (steam cracker, autothermal cracker). The hydrocarbon feed source does not have to be of a high purity of ethane. The feed stream may include ethane byproduct from a pyrolisis plant that might otherwise be recycled to the pyrolysis plant for further cracking to ethylene. Instead, this pyrolysis ethane can be fed to ethane ODH processes disclosed herein.

Figure 5:
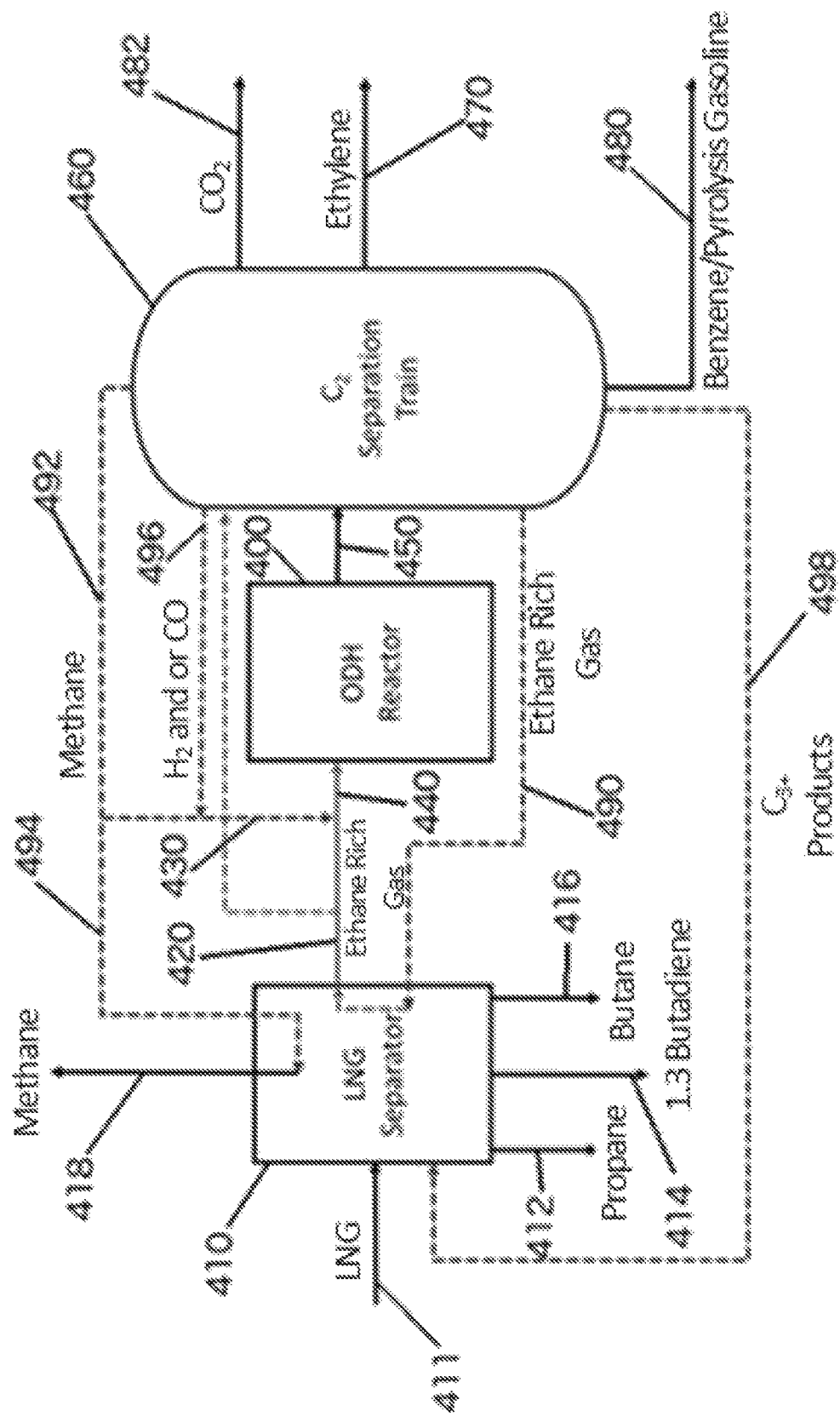
FIG. 5 is a schematic of one embodiment of an oxidative dehydrogenation (ODH) reactor integrated into a liquefied natural gas (LNG) separator.

FIG. 5 depicts an embodiment where the ODH reactor 400 is integrated within a liquified natural gas (LNG) separator 410. The ODH reactor 400 can have a variety of of configurations including the circulating fluidized-bed reactor or a packed bed reactor. The liquified natural gas stream 411 enters the LNG separator 410 and can be separated into a propane portion via line 412, a 1,3-butadiene portion via 414, a butane portion via 416, and/or a methane portion via 418. An ethane rich portion exits the LNG separator 410 to form the hydrocarbon feed stream 420. The hydrocarbon feed stream 420 is combined with a recycle feed stream 430 to form the reactor feed stream 440. The reactor feed stream 440 enters the ODH reactor 400 where it contacts an oxide-based redox catalyst to produce the product stream 450 containing ethylene and one or more byproducts such as methane, ethane, other byproducts, and mixtures thereof. The product stream 450 can enter the separation train 460 where the ethylene is separated via line 470. Other valuable products can be removed such as benzenes/pyrolysis gasoline via 480. The $CO_2$ produced can be separated via line 482. Unreacted ethane can be separated via line 490 and recycled back to the LNG separator 410 where it can be rejoined with the hydrocarbon feed stream 420. The methane can be separated via line 492 and all or part of the methane can be recycled into the recycle stream 430. A portion of the methane can be recycled via line 494 into the methane portion exiting the LNG separator 410 via line 418. $H_2$ and/or CO can be separated via line 496 into the recycle stream 430. The $C_{3+}$ byproducts such as propane and butane can be recycled to the LNG separator 410 via line 498.

Figure 6:
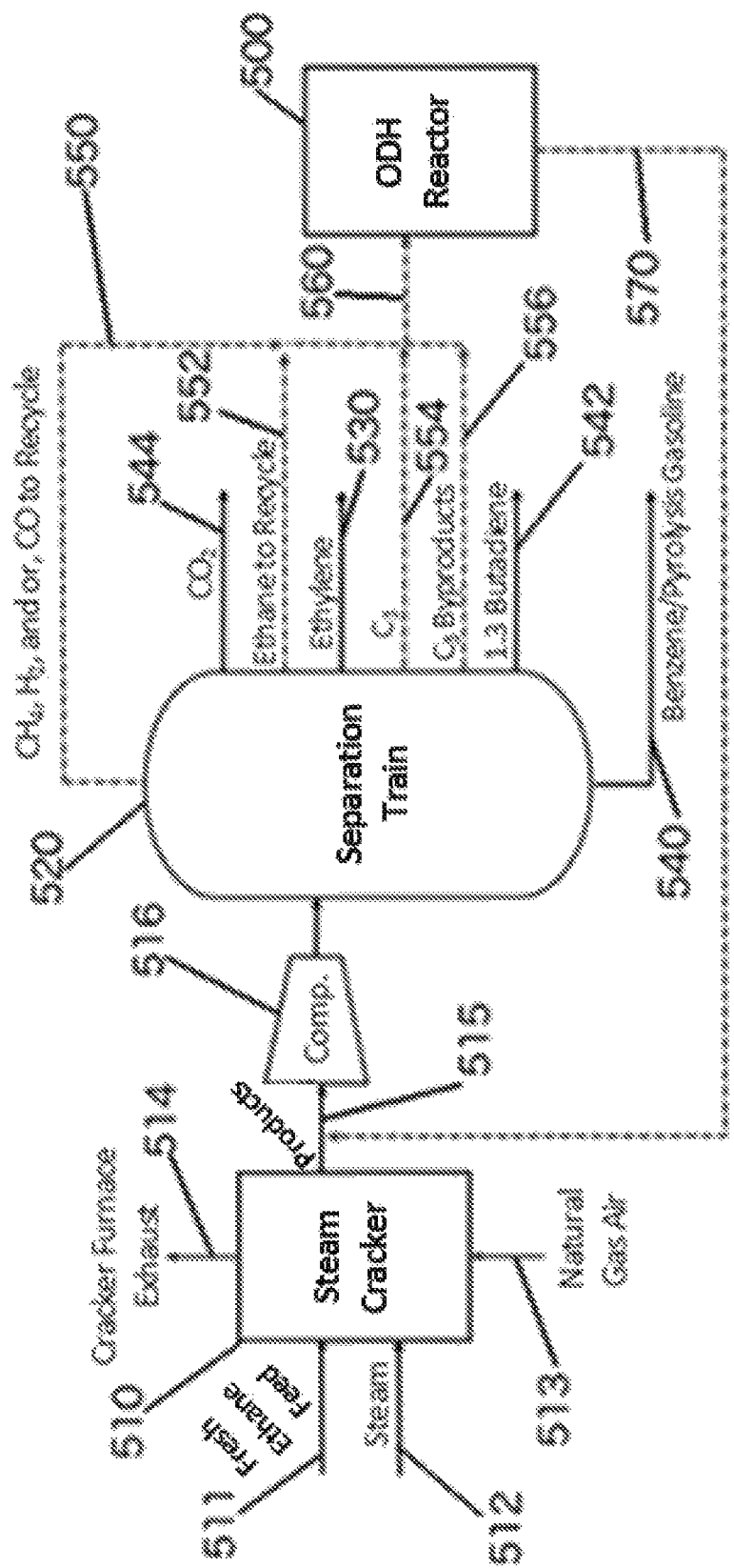
FIG. 6 is a schematic of one embodiment of an oxidative dehydrogenation (ODH) reactor integrated downstream of a conventional steam cracker.

FIG. 6 depicts an embodiment where the ODH reactor 500 is integrated with a standard steam cracker 510. An ethane-rich cracker feed stream 511 enters the steam cracker 510 and is combined with a steam source 512. Air and/or a fuel source such as natural gas can enter the steam cracker 510 via line 513. The cracker furnace exhaust can exit via line 514. The stream cracker products can exit the steam cracker 510 via line 515 and be compressed via a compressor 516 prior to entering the separation train 520. The ethylene can be separated in the separation train via 530. Other valuable products can be separated as well, such as benzenes and pyrolysis gasoline via line 540, 1,3-butadiene via line 542. Carbon dioxide can also be removed via line 544. All or part of the lighter byproducts such as methane, H2, and CO can be separate via 550, ethane via 552, C₃ byproducts via 554, and C₄ byproducts via 556 and all or part of each can be combined for the reactor feed stream 560. The reactor feed stream 560 enters the ODH reactor 500 where it can contact an oxide-based redox catalyst to produce the product stream 570 that can be combined with the products exiting the steam cracker 510 via 515 to be separated in the separation train 520.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

For the ODH sample 0.5 g of ODH catalyst was loaded into a ⅛" I.D. quartz u-tube and the remaining volume packed with inert 16 mesh white alumina grit. For the thermal cracking a u-tube of the same dimension was filled with only inert white alumina grit. The u-tubes were heated to 850° C. in a tube furnace. A gas flow control manifold was used to inject 10 standard ml of hydrocarbon gas into the reactor at a space velocity of 3000 h⁻¹. The mixture was 6.7% ° C. methane and 93.3 C % ethane along with dilution gas so that the hydrocarbon concentration was 80 volume %. The resultant product was collected in a gas sampling bag and analyzed with a gas chromatograph (GC). Using the amount of ethane and methane yield, the concentration of methane in the fresh feed that would give the inlet concentration of 6.7 C % at 100% recycle was calculated. In the case of thermal cracking it was determined that it was not possible for 100% methane recycle at any concentration of methane including 0%

For ethane/propane mixtures, sample of the same composition as described in were contacted with 10 standard ml of hydrocarbon at 850° C. and a space velocity of 3000 h⁻¹. The hydrocarbon was mixed so that it was 20 wt. % propane and 80 wt. % ethane, and diluted to 80% volume. The product gas was collected and analyzed with a GC. Based upon the yield of ethane and methane, and the measurements in table 1, the concentration of methane in fresh feed that would permit 100% methane recycle was extrapolated. In the case of thermal cracking it is not possible at any concentration of methane.

A comparison of the methane in the exit as a function of the methane in the feed is depicted in FIG. 1 for a traditional steam cracking and for an exemplary ODH reactor.

TABLE 1

Comparison of products the thermal cracking of ethane vs ODH of ethane at 850° C. and GHSV with 6.7% carbon methane in the reactor feed at 850° C., 3000 h⁻¹ GHSV, and 80% hydrocarbon feed, and the calculated maximum allowable methane feed concentration for 100% recycle to extinction.

|  | Thermal Cracking | ODH Catalyst |
|---|---|---|
| Methane Yield | 6.8% | 4.5% |
| Ethane Yield | 43.3% | 24.8% |
| Ethylene Yield | 47.0% | 59.6% |

TABLE 1-continued

Comparison of products the thermal cracking of ethane vs ODH of ethane at 850° C. and GHSV with 6.7% carbon methane in the reactor feed at 850° C., 3000 h⁻¹ GHSV, and 80% hydrocarbon feed, and the calculated maximum allowable methane feed concentration for 100% recycle to extinction.

|  | Thermal Cracking | ODH Catalyst |
|---|---|---|
| Methane in Recycle (Carbon basis) | 13.6% | 15.4% |
| Allowable Methane Content of fresh feed (Carbon basis) for extinction at 100% recycle | impossible | ≤3.1% |

TABLE 2

Comparison of products the thermal cracking of ethane vs ODH of 80/20 Wt. % ethane propane mix at reactor inlet at 850° C. and GHSV at 850° C., 3000 h⁻¹ GHSV, and 80% hydrocarbon feed, and extrapolated allowable methane content in fresh feed for 100% recycle to extinction. Example of Propane Rich Ethane Feed in Recycle 850

|  | Thermal Cracking | ODH |
|---|---|---|
| Methane Yield | 6.8% | 5.1% |
| Ethane Yield | 33.2% | 25.1% |
| Ethylene Yield | 52.6% | 59.3% |
| C3 Yield | 4.05% | 1.83% |
| C3 in Recycle | 9.18% | 5.71% |
| Methane in recycle (Carbon basis) | 15.45% | 15.86% |
| Expected Feed Methane concentration (Carbon basis) | Unfeasible (has to be a negative value) | ≤2.4% |

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method for the oxidative dehydrogenation of a hydrocarbon feed stream comprising ethane and one or both of methane and propane to produce a product stream comprising ethylene, the method comprising the steps of
combining a recycle stream comprising methane with the hydrocarbon feed stream to form a reactor feed stream;
contacting the reactor feed stream with an oxide-based redox catalyst to produce the product stream, wherein the product stream comprises ethylene, methane and one or more additional byproducts selected from the group consisting of ethane and other heavy hydrocarbons selected from the group consisting of C3 hydrocarbons and C4 hydrocarbons, and wherein the ethylene in the product stream is produced by simultaneously converting at least a part of both the ethane from the feed stream and the methane from the reactor feed stream into ethylene;
removing all or a part of the methane from the product stream to produce the recycle stream; and
wherein the hydrocarbon feed stream comprises about 1% to 15% methane,
wherein the method further comprises removing the heavy hydrocarbons from the product stream to produce the recycle stream; and
wherein at least 50% of the heavy hydrocarbons are recycled and converted to produce ethylene.

2. The method of claim 1, wherein at least 30% of the methane is recycled to produce ethylene and other valuable products.

3. The method of claim 1, wherein the yield of ethylene is higher than the yield of ethylene in the otherwise same system under the otherwise same conditions except where the methane is not recycled in the recycle stream.

4. The method of claim 1, wherein the hydrocarbon feed stream consists essentially of ethane and about 1% to about 15% methane.

5. The method of claim 1, wherein the hydrocarbon feed stream is from a liquefied natural gas separation unit.

6. The method of claim 1, wherein the hydrocarbon feed stream is from a stream cracker separation train.

7. The method of claim 1, wherein the oxide-based redox catalyst comprises an oxide having the formula $R_6R'O_8$, wherein each R and R' are selected from Mg, Mn, Fe, Ni, Al, Cr, Cu, and Co.

8. The method of claim 1, wherein the oxide-based redox catalyst is selected from the group consisting of $Mg_6MnO_8$, $Cu_6PbO_8$, and $Ni_6MnO_8$.

9. The method of claim 1, wherein the oxide-based redox catalyst comprises a promoter selected from the group consisting of Li, Na, B, Sm, Ga, Ti, W, Mo, V, Nb, Cr, K, Cs, Rb, P, and As.

10. The method of claim 1, wherein the byproducts comprise both methane and ethane;
    wherein the oxide-based redox catalyst is in a reactor comprising a separation train attached thereto and configured to receive the product stream;
    wherein the separation train separates the product stream into at least an ethylene stream, an ethane stream, and a methane stream; and
    wherein all or a part of the methane stream and the ethane stream are combined to produce the recycle stream.

11. The method of claim 10, wherein the reactor is a circulating fluidized bed reactor, a packed bed reactor, or a combination thereof.

12. The method of claim 10, wherein the reactor is at a temperature of about 850° C.

13. The method of claim 1, wherein the hydrocarbon feed stream comprises about 80% ethane.

14. The method of claim 10, wherein the hydrocarbon feed stream is injected into the reactor at a space velocity of about 3000 $h^{-1}$.

15. The method of claim 10, wherein the hydrocarbon feed stream is diluted to about 80% volume with a dilution gas before injection into the reactor.

16. The method of claim 1, wherein the hydrocarbon feed stream comprises about 93% ethane.

* * * * *